(12) United States Patent
Nandu et al.

(10) Patent No.: US 7,745,564 B2
(45) Date of Patent: Jun. 29, 2010

(54) SYSTEM FOR SYNTHESIS OF DEVICE FORMING MONOMERS

(75) Inventors: Mahendra Nandu, Pittsford, NY (US); Gary D. Friends, Ontario, NY (US); Mary Lou Friends, legal representative, Ontario, NY (US); David E. Seelye, Williamsville, NY (US); Vinod Kumar Kansal, Haryana (IN); C. C. Shah, Vadodara (IN); Dharmesh Balvantrai Mistry, Gujarat (IN)

(73) Assignee: Bausch & Lomb Incorporated, Rochester, NY (US)

( * ) Notice: Subject to any disclaimer, the term of this patent is extended or adjusted under 35 U.S.C. 154(b) by 922 days.

(21) Appl. No.: 11/471,991

(22) Filed: Jun. 21, 2006

(65) Prior Publication Data

US 2006/0293476 A1 Dec. 28, 2006

Related U.S. Application Data

(60) Provisional application No. 60/694,725, filed on Jun. 28, 2005.

(51) Int. Cl.
*C08G 73/10* (2006.01)
*A61F 2/16* (2006.01)
*C08F 226/02* (2006.01)

(52) U.S. Cl. .................. 528/322; 528/310; 528/502 C; 528/502 A; 528/502 D; 528/423

(58) Field of Classification Search ............. 528/502 C, 528/502 A, 502 D, 423, 322, 310; 359/159; 526/301; 556/437; 560/157; 623/6.11
See application file for complete search history.

(56) References Cited

U.S. PATENT DOCUMENTS

| 5,070,215 A | 12/1991 | Bambury et al. |
| 5,260,000 A | 11/1993 | Nandu et al. |
| 5,310,779 A | 5/1994 | Lai |
| 5,449,729 A | 9/1995 | Lai |
| 5,610,252 A | 3/1997 | Bambury et al. |
| 5,981,675 A | 11/1999 | Valint, Jr. et al. |
| 6,166,236 A | 12/2000 | Bambury et al. |

FOREIGN PATENT DOCUMENTS

| EP | 0 757 033 | 2/1997 |
| WO | WO01/00634 | 1/2001 |
| WO | WO2005/065734 | 7/2005 |

OTHER PUBLICATIONS

Moris, Gotor: "A novel and convenient route to 3'-carbonates from unprotected 2'-deoxynucleosides through an enzymatic reaction", *Journal of Organic Chemistry*, vol. 57, 1992, pp. 2490-2492.
Jaquadi, Selve, Dormoy, Castro, Martinez: "Le chloroformiate d'isopropenyle (IPCF) en chimie des amino-acides et des peptides—III Sythese d'esters actifs d'amino acides N'proteges", *Tetrahedron Letters*; vol. 26, 1985, pp. 1721-1722.

*Primary Examiner*—Duc Truong
(74) *Attorney, Agent, or Firm*—Glenn D. Smith

(57) ABSTRACT

Disclosed in embodiments herein is a method of synthesizing device forming monomers using N-(Vinyloxycarbonyloxy) succinimide.

2 Claims, No Drawings

SYSTEM FOR SYNTHESIS OF DEVICE FORMING MONOMERS

CROSS REFERENCE

This application claims the benefit of Provisional Patent Application No. 60/694,725 filed Jun. 28, 2005 and is incorporated herein by reference.

FIELD

This invention relates to novel methods of synthesizing medical device forming monomers.

BACKGROUND

Vinylchloroformate (VCF) is used as a starting raw material for the synthesis of many medical devices such as those disclosed in U.S. Pat. Nos. 5,310,779, 5,449,729, 5,610,252 and 6,166,236, the contents of which are incorporated herein by reference.

Vinylchloroformate is a toxic material and is difficult to transport by air. As described in the material data safety sheet provided by Aldrich Chemical Company, VCF has a flash point of 24° F. and when it is burning must be extinguished by the use of carbon dioxide, dry chemical powder or alcohol or polymer foam. In view of the safety difficulties encountered in using VCF, and its utility in forming highly useful medical devices, it would be desirable to provide a precursor useful in forming medical device forming monomers that is solid, less toxic and easy to store and ship.

Disclosed in embodiments herein are methods of using N-(Vinyloxycarbonyloxy)succinimide as a precursor molecule in making monomers useful in the formation of medical devices.

SUMMARY

Provided herein are methods of forming monomers for use in forming medical devices. Such medical devices would include contact lenses, phakic intraocular lenses, aphakic intraocular lenses, corneal implants, etc. These device forming monomers were previously synthesized with vinylchloroformate. Examples of compounds that can be synthesized by the method of the invention herein include Tris-VC (RD-325), Vinal acid (RD-594) and HEMA-VC (RD-678).

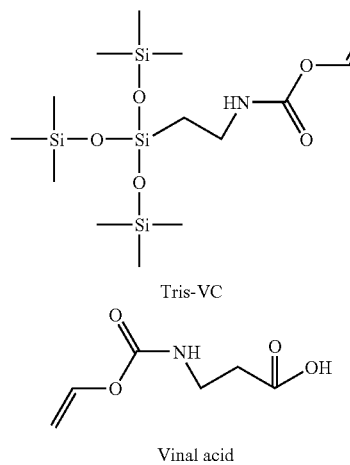

Tris-VC

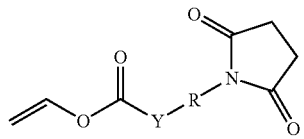

Vinal acid

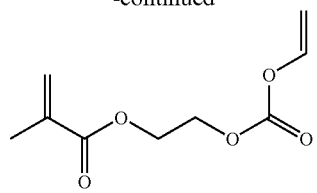

HEMA-VC

In one aspect the invention comprises reacting a succinimide compound having the following structural formula:

wherein R is an alkyl group of 0-6 carbons in length and Y is O or NH with a compound selected from the group consisting of amine or hydroxyl terminated acrylic compounds, amine or hydroxy terminated alkyl acrylic compounds, amine or hydroxyl terminated silane containing compounds and amine or hydroxyl terminated carboxylic acid containing compounds in a suitable solvent under conditions suitable to provide device forming monomers.

In yet another aspect of the invention HEMA-VC is synthesized by providing a reaction mixture comprising HEMA and pyridine in chloroform; adding drop wise N-(Vinyloxycarbonyloxy)succinimide in chloroform and reacting for a time sufficient to form a reaction mixture; washing the reaction mixture to form an organic layer and an aqueous layer; separating the organic layer from the aqueous layer; and, drying the organic layer to provide HEMA-VC.

In yet a further aspect of the invention vinal acid is synthesized by providing a mixture comprising N-(Vinyloxycarbonyloxy)succinimide and β-alanine in solvent; reacting for a time sufficient to form a reaction mixture; extracting the reaction mixture with ethylacetate; and drying, filtering and evaporating the extracted reaction mixture to provide vinal acid.

In still a further aspect of the invention carbamic acid, [3-[3,3,3-trimethyl-1,1-bis[(trimethylsilyl0oxy]disloxanyl] propy-, ethenyl ester (TRIS-VC) is synthesized by providing a reaction mixture of N-(Vinyloxycarbonyloxy)succinimide and 3-(aminopropyl)-tris-(trimethylsiloxy)silane in dichloromethane; stirring the reaction mixture for a time sufficient for the completion of the reaction; extracting the reaction mixture and removing the solvent to provide TRIS-VC.

DETAILED DESCRIPTION

Vinylchloroformate (VCF) is used as a starting raw material for the synthesis of many medical devices such as those disclosed in U.S. Pat. Nos. 5,310,779, 5,449,729, 5,610,252 and 6,166,236.

Vinylchloroformate is a toxic material and is difficult to transport by air. As described in the material data safety sheet provided by Aldrich Chemical Company, VCF has a flash point of 24° F. and when it is burning must be extinguished by the use of carbon dioxide, dry chemical powder or alcohol or polymer foam. In view of the safety difficulties encountered in using VCF, and its utility in forming highly useful medical devices, the inventors have discovered a method of synthesizing device forming monomers using as a monomer precursor a compound that is solid, less toxic and easier to store and ship than VCF.

It has been discovered that succinimide compounds can be used as precursors for the synthesis of device forming monomers that previously required VCF for their synthesis.

Succinimide forms of vinylcarbonate and vinyl carbamate contact lens material monomers are known. For example, U.S. Pat. No. 5,070,215 to Bambury et al. discloses the synthesis of N-(vinyloxycarbonyloxy)pyrrolidin-2,5-dione and N-[vinyloxycarbonyloxyethyl]pyrrolidin-2,5-dione however these molecules are described as being useful as comonomers rather than as precursors for monomers useful in forming medical devices.

Suitable succinimide compounds for use according to the invention herein would include those having the following structural formula:

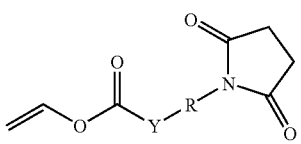

wherein R is an alkyl group of 0-6 carbons in length and Y is O or NH.

A generic reaction sequence according to the invention herein would include:

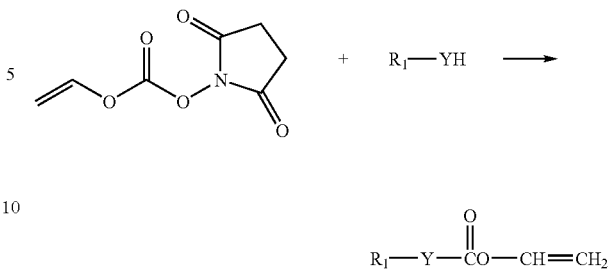

wherein $R_1$ is an acrylic radical or an alkyl acrylic radical and Y is as defined above.

The invention will be better understood by way of the following examples which are intended to illustrate but not limit the claims appended hereto.

EXAMPLES

Example 1

Synthesis of N-(Vinyloxycarbonyloxy)succinimide

Reaction Scheme:

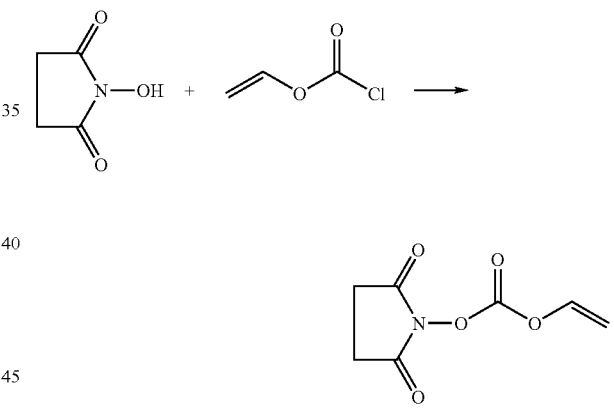

Raw Materials Required:

| No. | Raw material | MW | Wt gm(ml) | Moles | Molar ratio | Purity (%) | Source |
|---|---|---|---|---|---|---|---|
| 1 | VCF | 106.5 | 20.0, (17.2) | 0.18 | 1.0 | 97.0 | Paushak ltd |
| 2 | N-Hydroxy Succinimide | 115 | 25.9 | 0.22 | 1.2 | 98.0 | LR/Spectrochem |
| 3 | TEA | 101.2 | 20.8, (29.7) | 0.20 | 1.1 | 99.0 | LR/Samir tech |
| 4 | MDC | — | (150) | — | — | — | LR/SREnter. |
| 5 | DM Water | — | (120) | — | — | — | — |

Procedure:

To the stirred solution of N-hydroxy succinimide (25.9 g, 0.22 mol) and TEA (29.7 ml, 0.20 mol) in MDC (150 ml), VCF (17.2 ml, 0.18 mol) was added drop wise within 35 to 45 minutes, at −5 to 0° C., the reaction mixture was stirred further for 1 hr at 0° C. DM Water (120 ml) was added, the organic layer was separated from the aqueous layer and washed with brine (100 ml) and dried over anhydrous sodium sulfate. Removal of solvent from organic layer using a rotavapor provided product separated as gummy liquid. This product was turned to white solid on keeping at room temp for 30 min. MP: 60-61° C. Yield 24.0 gm (70%). The structure of the final product was confirmed by PMR & Mass spectrum.

Example 2

Synthesis of 2-Methacryloxyethyl vinyl carbonates (HEMA-VC)

Reaction Scheme:

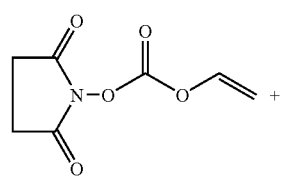

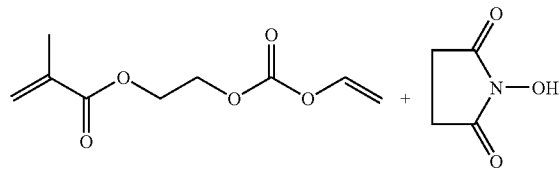

Raw Material Required:

| No | Raw material | MW | Wt. gm, (ml) | Moles | Molar ratio | % Purity |
|---|---|---|---|---|---|---|
| 1 | 2-Hydroxy ethyl methacrylate (HEMA) | 130.1 | 13.43, (12.5) | 0.103 | 1.0 | 96 |
| 2 | N-(Vinyloxycarbonyloxy) succinimide | 185 | 10.0 | 0.054 | 0.523 | — |
| 3 | Pyridine | 79.1 | 7.5, (7.6) | 0.0938 | 0.918 | 99 |
| 4 | CHCl₃ | — | 100 ml | — | — | — |

Procedure:

To the stirred solution of HEMA (13.4 g, 0.10 mol), pyridine (7.5 g, 0.09 mol) in chloroform (60 ml), N-(Vinyloxycarbonyloxy)succinimide (10.0 g, 0.054 mol) in chloroform (40 ml) was added drop wise at 0-5° C. The temperature was then allowed to rise to ambient (25-28° C.) and stirring was continued further for 14 hrs. The reaction mixture was washed twice with 150 ml 2N HCl, once with 70 ml brine, and twice with 150 ml 2N NaOH. The organic layer was dried over anhydrous sodium sulfate and then filtered. The solvent was removed on rotary evaporator with maximum temp 40° C. The residue was distilled after addition of 100 ppm 2,5-diphenylbenzoquinone and 100 ppm CuCl to the pot before distillation to give 5.4 g (BP: 80-84° C./3-6 mm Hg) HemaVC. 50 ppm of 1,1'-binaphthol was added as inhibitor to the distilled HemaVC. (Yield:—minimum 25.0%). PMR confirms the structure.

Example 3

Synthesis of N-(Vinyloxycarbonyl)-β-alanine (Vinal Acid; RD-594)

Reaction Scheme:

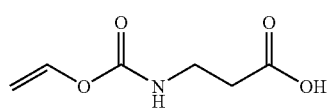

Raw Material Required:

| No. | Raw material | MW | Wt in gm, (ml) | Moles | Molar ratio | % Purity | Sources |
|---|---|---|---|---|---|---|---|
| 1 | N-(Vinyloxycarbonyloxy)succinimide | 185 | 10.0 | 0.054 | 1.0 | — | 465/31 |
| 2 | β-alanine | 89 | 7.2 | 0.081 | 1.5 | 98.0 | Spect/LR |
| 3 | Sodium carbonate | 106 | 11.44 | 0.108 | 2.0 | 99.5 | Samir/LR |
| 4 | THF | — | (60) | — | — | 99.5 | Samir/LR |
| 5 | DM Water | — | (50) | — | — | — | — |

Procedure:

To a 250 ml round bottom flask equipped with a mechanical stirrer, a thermometer pocket and a dropping funnel was added (7.2 g 0.081 mol) of β-alanine, (11.4 g, 0.108 mol) of sodium carbonate and 50 ml DM Water. The dropping funnel was charged with (10.0 g, 0.054 mol) of N-(Vinyloxycarbonyloxy)succinimide and 60 ml THF. With rapid stirring, the N-(Vinyloxycarbonyloxy)succinimide in THF was added drop wise over 25 minutes. The reaction mixture was stirred for 48 hrs at room temperature. The pH probe was placed in the reaction pot, the stirrer speed kept slow and the solution was brought to pH 1.0 with 12N HCl. The reaction mixture was extracted twice with 100 ml portions of ethyl acetate. The combined ethyl acetate extracts dried with sodium soleplate, filtered and the solvent was removed on a rotary evaporator at 50° C. (20 mm Hg) to get desired product as white solid. (Yield ~40%). Structure of the product was confirmed by PMR & Mass spectra.

Example 4
Synthesis of N-(Vinyloxycarbonyl)-3-amino-propyl-tris(trimethylsiloxy silane) (Tris-VC) (RD-325)

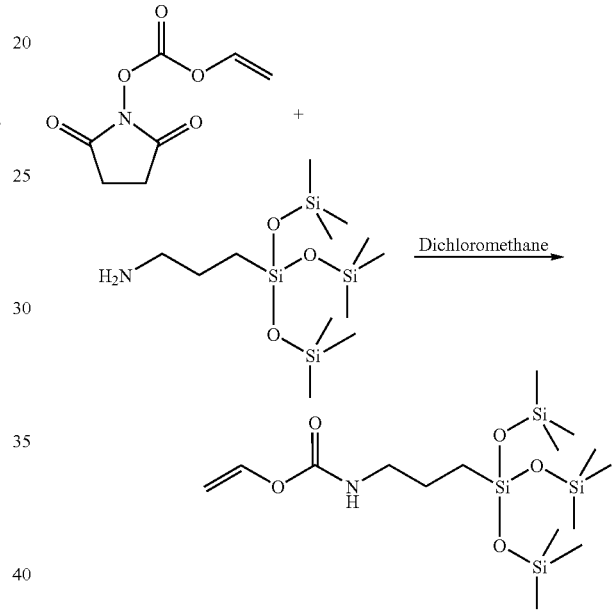

| No | Raw material | MW | Wt. (gm)/(ml) | Moles | Mole ratio Tris-amine/NVS | % Purity |
|---|---|---|---|---|---|---|
| 1. | N-(Vinyloxycarbonyloxy)-succinimide (NVS) | 185.0 | 2.22 gm | 0.012 | 1.2 | — |
| 2. | 3-aminopropyl-tris-(trimethylsiloxy) silane (Tris-amine) | 353.76 | 3.538 gm | 0.010 | 1.0 | 99.3 (B&L) |
| 3. | Methylene dichloride (MDC) | — | 80.0 ml | — | — | — |

To the stirred solution of N-(Vinyloxycarbonyloxy)succinimide (2.22 g; 0.012 moles) in dichloromethane (40.0 ml) at 0° C., a solution of 3-aminopropyl-tris-(trimethylsiloxy)silane (3.538 g; 0.010 moles) in dichloromethane (40.0 ml) was added drop wise over 15 minutes. After stirring the resulting mixture for 1.5 h, TLC showed the completion of the reaction. The reaction mixture was extracted with 2N HCl, (150.0 ml), 2N NaOH (150.0 ml) and brine (150.0 ml). The dichloromethane layer was dried over anhydrous sodium sulfate and subjected to solvent removal to yield turbid oil. The turbid oil was taken in hexane (75.0 ml) and passed through a celite bed. Distillation of the solvent furnished the required product as a colorless oil (3.70 g) (87% Yield). Purity by HPLC: 98.8%.

Example 5

Synthesis of N-(Vinyloxycarbonyl)-β-alanine Using N-(Vinyloxycarbonyloxy)succinimide To a 250 ml round bottom flask equipped with mechanical stirrer, a thermometer pocket and a dropping funnel was added β-alanine (2.82 g 0.031 mol), sodium carbonate (4.85 g, 0.046 mol) and DM Water (40 ml). The dropping funnel was charged with N-(Vinyloxycarbonyloxy)succinimide (4.0 g, 0.021 mol) and THF (30 ml). Under rapid stirring, N-(Vinyloxycarbonyloxy)succinimide in THF (20 ml) was added drop wise over 25 minutes. The reaction mixture was stirred for 14 hrs at room temp. The pH probe was then inserted into the reaction pot & the solution was brought to pH 1.0 with 12N HCl. The reaction mixture was extracted with ethylacetate (50 ml×2). The combined ethylacetate extracts were dried over anhydrous sodium sulfate, filtered and the solvent was removed on a rotavapor at 50° C. (20 mm Hg) to get desired product as white solid. (Yield~42%). Purity by HPLC: 97.0%. $^1$HNMR (CDCI$_3$).δ.2.64(2H,t,CH$_2$CO),3.51 (2H,t,NHCH$_2$), 4.45 (1H,dd, =CH$_2$),4.76(1H,dd,=CH$_2$), 5.48(1H,s,—NH),7.19(1H,dd,=CH). The mass spectra shows the M+1 peak at 159.9 m/e.

Example 6

Synthesis of N-(Vinyloxycarbonyl)-β-alanine Using N-(Vinyloxycarbonyloxy)succinimide To a 250 ml round bottom flask equipped with mechanical stirrer, a thermometer pocket and a dropping funnel was added β-alanine (7.2 g 0.081 mol), sodium carbonate (11.4 g, 0.108 mol) and DM Water (50 ml). The dropping funnel was charged with N-(Vinyloxycarbonyloxy)succinimide (10.0 g, 0.054 mol) and THF (60 ml). Under rapid stirring, the N-(Vinyloxycarbonyloxy)succinimide in THF (20 ml) was added drop wise over 25 minutes. The reaction mixture was stirred for 48 hrs at room temp. The pH probe was placed in the reaction pot, and the solution was brought to pH 1.0 with 12N HCl. The reaction mixture was extracted with ethylacetate (100 ml×2). The combined ethylacetate extracts was dried over anhydrous sodium sulfate, filtered and the solvent was removed on a rotavapor at 50° C. (20 mm Hg) to get desired product as white solid. (Yield~57%). Purity by HPLC: 97.5%. $^1$HNMR (CDCI$_3$).δ.2.64(2H,t, CH2CO), 3.51(2H,t, NHCH$_2$), 4.45 (1H,dd, =CH$_2$),4.76(1H,dd,=CH$_2$),5.48 (1H,s,—NH),7.19(1H,dd,=CH). The mass spectra shows the M+1 peak at 159.9 m/e.

Example 7

Synthesis of 2-Methacryloxy ethyl vinylcarbonate Using N-(Vinyloxycarbonyloxy)succinimide To the stirred solution of HEMA (7.0 g, 0.053 mol), pyridine (3.9 g, 0.048 mol) in chloroform (50 ml), N-(Vinyloxycarbonyloxy)succinimide (5.1 g, 0.027 mol) in chloroform (20 ml) was added drop wise at 0-5° C. The temperature was then allowed to rise to ambient (25-28° C.) and stirring was continued further for 14 hrs. The reaction mixture was washed with 2N HCl (75 ml×2), brine (50 ml), and 2N NaOH (75 ml×2). The organic layer was dried over anhydrous sodium sulfate and then filtered. The solvent was removed on rotavapor with maximum temp 40° C. The residue was distilled after addition of 2,5-diphenylbenzoquinone (100 ppm) and CuCl (100 ppm) to the pot (BP: 80-84° C./3-6 mm Hg) to give HemaVC (Yield ~56%). 1,1'-binaphthol (50 ppm) was added as inhibitor to the distilled HemaVC. Purity by HPLC: 91%. $^1$H NMR (CDCI$_3$). δ.1.89(3H,s,—CH$_3$),4.33(4H,m,—O—CH$_2$—CH$_2$—O—),4.53(1H,dd,=CH$_2$),4.86(1H, dd,=CH$_2$),5.55(1H,s,=CH$_2$),6.09(1H,s, =CH$_2$),6.98(1H dd,—CH=CH$_2$).

The mass spectrum shows M$^+$ peak at 200.1 m/e.

Example 8

Synthesis of 2-Methacryloxy ethyl vinylcarbonate Using N-(Vinyloxycarbonyloxy)succinimide To the stirred solution of HEMA (4.21 g, 0.032 mol), N-Methyl morpholine (2.0 g, 0.02 mol) in dichloromethane (50 ml), N(Vinyloxycarbonyloxy)succinimide (5.0 g, 0.027 mol) in chloroform (20 ml) was added drop wise at 0-5° C. The temperature was then allowed to rise to ambient (25-28° C.) and stirring was continued further for 14 hrs. The reaction mixture was washed with 2N HCl (50 ml×2), brine (50 ml), and 2N NaOH (50 ml×2). The organic layer was dried over sodium sulfate and then filtered. The solvent was removed on a rotavapor with maximum temp 40° C. The residue was distilled after addition of 2,5-diphenylbenzoquinone (100 ppm) and CuCl (100 ppm) to the pot to give HemaVC (Yield~40%) (BP: 80-84° C./3-6 mm Hg). 1,1'-binaphthol (50 ppm) was added as inhibitor to the distilled HemaVC. Purity by HPLC: 82.3%. $^1$H NMR (CDCI$_3$). δ.1.89(3H,s,—CH$_3$),4.33(4H,m,—O—CH$_2$—CH$_2$—O—),4.53(1H,dd, =CH$_2$),4.86(1H,dd,=CH$_2$),5.55(1H,s,=CH$_2$),6.09(1H,s, =CH$_2$),6.98(1H,dd,—CH=CH$_2$). The mass spectra shows M$^+$ peak at 200.1 m/e.

Example 9

Synthesis of carbamic acid, [3-[3,3,3-trimethyl-1,1-bis[(trimethylsilyl0oxy]disloxanyl]propy-, ethenyl ester (Tris-VC)

I.

To a 250 mL 3-neck round bottom flask fitted with a magnetic stirrer, a dropping funnel, a guard tube and an ice bath, was added N-(Vinyloxycarbonyloxy)succinimide (4.625 g, 25 mmol), pyridine (0.5 mL, 6.25 mmol) and dichloromethane (40.0 ml). To the resulting ice cold solution thus formed, a solution of 3-aminopropyl-tris-(trimethylsiloxy) silane (8.844 g, 25 mmol) in dichloromethane (40.0 ml) was added in a drop wise manner under magnetically stirred condition during 30 minutes. After the addition was over, the mixture was stirred magnetically for one and half-hour. Completion of the reaction was monitored by TLC. The reaction mixture was brought to room temperature and washed with 2N HCl, (150.0 ml), 2N NaOH (150.0 ml) and brine (150.0 ml). The dichloromethane layer was dried over anhydrous sodium sulfate and subjected to solvent removal to yield turbid oil. The turbid oil was taken in hexane (100.0 ml) and passed through a celite bed. Distillation of the solvent furnished the required product as a colorless oil (9.60 g, 92% Yield). Purity by HPLC: 96.0%.

$^1$H NMR (CDCl$_3$) δ 0.10 (27H, s, [OSi(CH$_3$)$_3$]$_3$), δ 0.46 (2H, t, CH$_2$), δ 1.56 (2H,q., CH$_2$), δ 3.19 (2H,q., CH$_2$), δ 4.41 (1H, d, vinyl CH), δ 4.72 (1H, d, vinyl CH), δ 4.97 (1H, bs NH) and δ 7.22 (1H,q., vinyl CH). The $^1$H NMR spectral Analysis was consistent with the proposed chemical structure.

II.

To a 100 mL 3-neck round bottom flask fitted with a magnetic stirrer, dropping funnel, guard tube and an ice bath, was added N-(Vinyloxycarbonyloxy)succinimide (1.85 g, 10 mmol), triethylamine (1.39 mL, 10 mmol) and dichloromethane (20.0 mL). To the resulting ice cold solution thus formed, a solution of 3-aminopropyl-tris-(trimethylsiloxy) silane (3.5376 g, 10 mmol) in dichloromethane (20.0 ml) was added in a drop wise manner under magnetically stirred condition during 15 minutes. After the addition was over, the mixture was stirred magnetically for one and a half-hour. Completion of the reaction was monitored by TLC. The reaction mixture was brought to room temperature and washed with 2N HCl, (70.0 ml), 2N NaOH (70.0 ml) and brine (50.0 ml). The dichloromethane layer was dried over anhydrous sodium sulfate and subjected to solvent removal to yield turbid oil. The turbid oil was taken in hexane (50.0 ml) and passed through a celite bed. Distillation of the solvent furnished the required product as a colorless oil (3.14 gm, 74.1% Yield). Purity by HPLC: 86.1%.

$^1$H NMR (CDCl$_3$) δ 0.10 (27H, s, [OSi(CH$_3$)$_3$]$_3$), δ 0.46 (2H, t, CH$_2$), δ 1.56 (2H,q., CH$_2$), δ 3.19 (2H,q., CH$_2$), δ 4.41 (1H, d, vinyl CH), δ 4.72 (1H, d, vinyl CH), δ 4.97 (1H, bs NH) and δ 7.22 (1H,q., vinyl CH). The $^1$H NMR spectral Analysis was consistent with the proposed chemical structure.

III. (Mole ratio: N-(Vinyloxycarbonyloxy)succinimide/3-(Aminopropyl)-tris-(trimethylsiloxy)silane=1.5/1)

To a 100 mL 3-neck round bottom flask fitted with a magnetic stirrer, dropping funnel, guard tube and an ice bath, was added N-(Vinyloxycarbonyloxy)succinimide 2.775 g (15 mmol) and dichloromethane 40.0 mL. To the resulting ice cold solution thus formed a solution of 3-aminopropyl-tris-(trimethylsiloxy)silane 3.5376 g (10 mmol) in dichloromethane 40.0 mL was added in a drop wise manner under magnetically stirred condition during 15 minutes. After the addition was over, the mixture was stirred magnetically for one and a half-hour. Completion of the reaction was monitored by TLC. The reaction mixture was brought to the room temperature and washed with 2N HCl, (70.0 mL), 2N NaOH (70.0 mL) and brine (50.0 mL). The dichloromethane layer was dried over anhydrous sodium sulfate and subjected to solvent removal to yield turbid oil. The turbid oil was taken in hexane (50.0 mL) and passed through a celite bed. Distillation of the solvent furnished the required product as a colorless oil (3.9 g) (92% Yield). Purity by HPLC: 98.8%.

$^1$H NMR (CDCl$_3$) δ 0.10 (27H, s, [OSi(CH$_3$)$_3$]$_3$), δ 0.46 (2H, t, CH$_2$), δ 1.56 (2H,q., CH$_2$), δ 3.19 (2H,q., CH$_2$), δ 4.41 (1H, d, vinyl CH), δ 4.72 (1H, d, vinyl CH), δ 4.97 (1H, bs NH) and δ 7.22 (1H,q., vinyl CH). The $^1$H NMR spectral Analysis was consistent with the proposed chemical structure.

TABLE-I

Synthesis of Vinal acid from N-(Vinyloxycarbonyloxy) succinimide and β-alanine.

| No | NVS** gm (mole) | β-alanine gm (mole) | Sodium carbonate (wt) (mole) | DM water (ml) | Solvent (ml) | Reaction time (Hr) | Vinal acid (gm) (% yield) | % Purity by HPLC |
|---|---|---|---|---|---|---|---|---|
| 1 | 4 (0.021) | 2.8 (0.031) | 4.85 | 40 | THF (30) | 14 | 1.4 (42) | 97 |
| 2 | 5 (0.027) | 7.2 (0.081) | Nil | 10 | THF (30) | 1.2 | 8.4 (75.5) | 94 |
| 3 | 4 (0.021) | 3.7 (0.042) | 2.22 (0.021) | 20 | Acetone (35) | 48 | — | — |
| 4 | 5 (0.027) | 2.4 (0.027) | 5.0* (0.057) | Nil | MDC (120) | 4 | — | — |
| 5 | 10 (0.054) | 7.2 (0.081) | 11.44 (0.108) | 50 | THF (60) | 48 | 7.0 (57.3) | 97.5 |
| 6 | 10 (0.054) | 9.6 (0.107) | 5.72 (0.054) | 15 | THF (60) | 12 | 6.8 (42) | 97.6 |

*TEA has been used in place of sodium carbonate
**NVS: —N-(Vinyloxycarbonyloxy)succinimide

TABLE-II

Synthesis of Hema-VC from N-(Vinyloxycarbonyloxy)succinimide and Hydroxyethylmethacrylate.

| No | HEMA* (gm) (mole) | NVS (gm) (mole) | Solvent (ml) | Base (ml) (mole) | Reaction time (Hr) | Hema-VC (gm) (% yield) | Purity (% by GC) |
|---|---|---|---|---|---|---|---|
| 1 | 5 (0.038) | 7.1 (0.038) | MDC** (50) | Pyridine 3.3 (0.42) | 21 | — | — |
| 2 | 13.4 (0.1) | 10 (0.054) | Chloroform (100) | Pyridine 7.5 (0.09) | 14 | 8.47 (41) | 86.24 |
| 3 | 8 (0.061) | 13.6 (0.073) | MDC (70) | Nil | 24 | — | — |
| 4 | 7 (0.053) | 5.1 (0.027) | Chloroform (70) | Pyridine 3.9 (0.048) | 14 | 6 (56) | 91 |
| 5 | 4.57 (0.035) | 5 (0.027) | Ethyl acetate (45) | TEA*** 3.8 (0.048 | 22 | — | — |

TABLE-II-continued

Synthesis of Hema-VC from N-(Vinyloxycarbonyloxy)succinimide and Hydroxyethylmethacrylate.

| No | HEMA* (gm) (mole) | NVS (gm) (mole) | Solvent (ml) | Base (ml) (mole) | Reaction time (Hr) | Hema-VC (gm) (% yield) | Purity (% by GC) |
|---|---|---|---|---|---|---|---|
| 6 | 4.21 (0.032) | 5 (0.027) | MDC (50) | NMM**** 2 (0.02) | 31 | 3 (40) | 82.33 |

*HEMA: Hydroxyethylmethacrylate
**MDC: Methylenedichloride
***TEA: Triethyl amine
****NMN: N-Methylmorpholine
*****Reaction was carried out at 45-65° c.

TABLE-III

Synthesis of Tris-VC from N-(Vinyloxycarbonyloxy)succinimide and Tris-amine.

| No. | Tris-amine* (gm) (mole) | NVS (gm) (mole) | Solvent (ml) $CH_2Cl_2$ | Base ml (mol) | Mole ratio Tris-amine/NVS/Base | Reaction time (Hr) | Tris-VC** gm (% Yield) | Purity by GC |
|---|---|---|---|---|---|---|---|---|
| 1. | 8.844 (0.025) | 4.625 (0.025) | 80.0 | Pyridine 1.01 (0.0125) | 1:1:0.5 | 3 | 8.6 (81) | 97% |
| 2. | 8.844 (0.025) | 4.625 (0.025) | 80.0 | Pyridine 0.5 (0.00625) | 1:1:0.25 | 3 | 9.6 (92) (Crude) | 96% |
| 3. | 3.5376 (0.01) | 1.85 (0.01) | 40.0 | TEA 1.39 (0.01) | 1:1:1 | 2.25 | 3.14 (74.1) | 86.1% |
| 4. | 3.5376 (0.01) | 2.775 (0.015) | 80.0 | — | 1.5:1 | 2.5 | 3.7 (87) | 89.9% |
| 5. | 3.5376 (0.01) | 2.775 (0.015) | 80.0 | — | 1.5:1 | 2 | 3.9 (92) | 98.8% |
| 6. | 111.067 (0.3140) | 69.7 (0.3768) | 500.0 | — | 1.2:1 | 2.5 | 123 (92) | 98% |

*Tris-amine: 3-aminopropyl-tris-(trimethylsiloxy)silane
**Tris-VC: N-(Vinyloxycarbonyl)-3-aminopropyltris(trimethylsiloxy silane)
***Cooling is necessary during addition of the reagents The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others. For example, Although the examples used N-hydroxy succinimide to react with VCF to form the precursor compounds, it is envisioned that other reactive species such as 4-nitophenol and pentafluorophenol would be useful in forming monomer precursor molecules. Other compounds that when reacted with an acid chloride such as VCF to provide the corresponding active ester or active amide may also be useful.

What is claimed is:

1. A method of synthesizing N-(Vinyloxycarbonyl)-3-amino-propyltris(trimethylsiloxy silane), the method comprising:

providing a reaction mixture of N-(Vinyloxycarbonyloxy)succinimide and 3-aminopropyl-tris-(trimethylsiloxy)silane in dichloromethane; s stirring the reaction mixture for a time sufficient for the completion of the reaction; and, extracting the reaction mixture and removing the solvent to provide N-(Vinyloxycarbony)-3-amino-propyltris(trimethylsiloxy silane) VC.

2. The method of claim 1 wherein the N-(Vinyloxycarbony)-3-amino-propyltris(trimethylsiloxy silane) is optically clear.

* * * * *